US009981001B2

(12) United States Patent
Del Vecchio

(10) Patent No.: US 9,981,001 B2
(45) Date of Patent: May 29, 2018

(54) METHOD, APPARATUS AND COMPOSITIONS FOR THE PROPHYLAXIS AND TREATMENT OF COLONY COLLAPSE DISORDER

(75) Inventor: Francesca Del Vecchio, Rome (IT)

(73) Assignee: Healthy Bees, LLC., West Palm Beach, FL (US)

( * ) Notice: Subject to any disclaimer, the term of this patent is extended or adjusted under 35 U.S.C. 154(b) by 934 days.

(21) Appl. No.: 14/239,988

(22) PCT Filed: Mar. 14, 2012

(86) PCT No.: PCT/IT2012/000073
§ 371 (c)(1),
(2), (4) Date: Apr. 1, 2014

(87) PCT Pub. No.: WO2013/030854
PCT Pub. Date: Mar. 7, 2013

(65) Prior Publication Data

US 2014/0212520 A1 Jul. 31, 2014

(30) Foreign Application Priority Data

Aug. 26, 2011 (IT) ............................ RM2011A0450

(51) Int. Cl.

| | |
|---|---|
| *A61K 36/886* | (2006.01) |
| *A01K 51/00* | (2006.01) |
| *A01K 53/00* | (2006.01) |
| *A61K 36/185* | (2006.01) |
| *A61K 36/53* | (2006.01) |
| *A61K 36/88* | (2006.01) |
| *A23K 20/105* | (2016.01) |
| *A23K 20/147* | (2016.01) |
| *A23K 20/163* | (2016.01) |
| *A23K 20/10* | (2016.01) |
| *A23K 50/90* | (2016.01) |

(52) U.S. Cl.
CPC ............ *A61K 36/886* (2013.01); *A01K 51/00* (2013.01); *A01K 53/00* (2013.01); *A23K 20/10* (2016.05); *A23K 20/105* (2016.05); *A23K 20/147* (2016.05); *A23K 20/163* (2016.05); *A23K 50/90* (2016.05); *A61K 36/185* (2013.01); *A61K 36/53* (2013.01); *A61K 36/88* (2013.01); *Y02P 60/70* (2015.11)

(58) Field of Classification Search
None
See application file for complete search history.

(56) References Cited

U.S. PATENT DOCUMENTS 6,096,350 A * 8/2000 Kemp .................... A01N 59/00
424/661
7,597,912 B2 * 10/2009 Probasco .............. A01K 51/00
424/737
2007/0026765 A1 2/2007 Renn
2009/0209499 A1 * 8/2009 Orban ................. A61K 31/616
514/159
2010/0074976 A1 * 3/2010 Fowler ..................... A23L 2/52
424/745

FOREIGN PATENT DOCUMENTS

| | | | | |
|---|---|---|---|---|
| CN | 1227465 | A | 9/1999 |
| CN | 1830262 | A | 9/2006 |
| CN | 101278681 | A | 10/2008 |
| EP | 2 272 332 | A2 | 1/2011 |
| EP | 2 272 332 | A2 | 1/2011 |
| WO | 97/47193 | A1 | 12/1997 |
| WO | WO 2008/132524 | A1 | 11/2008 |
| WO | WO 2009/082659 | A2 | 7/2009 |
| WO | WO 2009/135289 | A1 | 11/2009 |

OTHER PUBLICATIONS

LeBlanc (J. Agric. Food Chem. (2008), vol. 56, pp. 8565-8573).*
Diana Sammataro et al., "Feeding essential oils and 2-heptanone in sugar syrup and liquid protein diets to honey bees (*Apis mellifera* L.) as potential Varroa mite (*Varroa destructor*) controls," Journal of Apicultural Research and Bee World, vol. 48, No. 4, pp. 256-262, Jul. 30, 2009.
Ahmed H. Fouly et al., "Evaluation of Infestation Levels of the Ectoparasitic Mite *Varroa destructor* Infesting Honey bee *Apis mellifera* and its Control Usig Essential Oil in Qassim Region, Saudi Arabia," Journal of Entomology, vol. 6, No. 3, pp. 135-144, Jul. 2009.

(Continued)

*Primary Examiner* — Susan Hoffman

(74) *Attorney, Agent, or Firm* — Arent Fox LLP

(57) ABSTRACT

This invention concerns a method for preventing and treating Colony Collapse Disorder, consisting in the use of an automated device that delivers a diet specifically calibrated for consumption by farm colonies of bees to be treated. The apparatus comprises a box-like container (10) accommodating in its interior at least one reservoir for liquid-tight, accessible from outside through a nozzle (4), an atomizing device of a liquid solution or suspension contained in the reservoir, means for the delivery (2, 1) of the liquid atomized solution or suspension into micrometric drops outside the apparatus, and a control unit programmed for timing the delivery of the solution or suspension to the outside, for the determination of the quantity of solution or suspension delivered and for emitting alarm signals in case of malfunction, the apparatus being powered DC with the energy supplied by a solar panel (5) located outside of the container.

The liquid solution or suspension comprises tonic and nutrient ingredients, mainly consisting of milk powder, sugars and lower organic acids, antioxidant and antiseptic ingredients contained in plant extracts and healing ingredients to bees, such as essential oils of thyme and oxalic acid.

7 Claims, 2 Drawing Sheets

(56) References Cited

OTHER PUBLICATIONS

Fernando Leite Cardoso et al., "Análise sazonal do potencial antimicrobiano e teores de flavonoides e quinonas de extratos foliares de Aloe arborescens Mill., Xanthorrhoeaceae," Biosciences Information Service, Philadelphia, PA, Brazilian Journal of Pharmacognosy, vol. 20, No. 1, pp. 35-40, Jan./Mar. 2010.

Tytti Kujala et al., "Betalains and Phenolics in Red Beetroot (*Beta vulgaris*) Peel Extracts: Extraction and Characterisation," Biosciences Information Service, Philadelphia, PA, May 2001, pp. 343-348.

Stella A. Ordoudi et al., "Further Examination of Antiradical Properties of Crocus *sativus* Stigmas Extract Rich in Crocins," Journal of Agricultural and Food Chemistry, vol. 27, No. 8, pp. 3080-3086, Apr. 2009.

Mydola H. Haydak, "Honey Bee Nutrition," Annual Review of Entomology, vol. 15, No. 1, pp. 143-156, Jan. 1, 1970.

Kalle Toomemaa et al., "The effect of different concentrations of oxalic acid in aqueous and sucrose solution on *Varroa* mites and honey bees," Apidologie, vol. 41, pp. 643-653, Nov. 2010.

\* cited by examiner

METHOD, APPARATUS AND COMPOSITIONS FOR THE PROPHYLAXIS AND TREATMENT OF COLONY COLLAPSE DISORDER

CROSS-REFERENCED TO RELATED APPLICATIONS

This application is a U.S. national phase application of the International Patent Application No. PCT/IT2012/000073, filed Mar. 14, 2012, and published in the English language, pending, which claims the benefit of Italian Patent Application No. RM2011A000450, filed Aug. 26, 2011, in a language other than English, the disclosure of the prior applications being incorporated in their entirety by reference.

TECHNICAL FIELD

The present invention concerns a method for preventing and treating Colony Collapse Disorder, an apparatus for implementing such a method and the nutritious and therapeutic compositions to be distributed to the bees to be treated by this method. More specifically, the invention relates to a device that dispenses, in an automated way, a specifically calibrated diet for consumption by one or more colonies of domesticated honey bees, in substitution or in addition to natural nourishment that the insects derive from their normal activity of collecting and processing nectar, pollen and other natural materials. The consumption of nutrients and therapeutics according to the method proposed helps the treated bees to resist the disease known as "Colony Collapse Disorder".

BACKGROUND OF THE INVENTION

Bees are the kind of social insects most appreciated and studied since antiquity, whose usefulness is certainly known since prehistoric times. As other insects in the family of Apidae, bees collect nectar and pollen to feed their offspring and to store them in their combs as food storage.

While it is not the only group of pollinators (insects which, with their activities, carry pollen from flower to flower allowing pollination and the subsequent formation of the fruit), honey bees are undoubtedly the most important one for humans, also for the various products that their colonies develop from nectar and other materials collected by foraging, including not only honey, but also beeswax, propolis, royal jelly. Unlike other social apidae like bumblebees, which perform similar functions as pollinators useful to agriculture but most of which do not survive the winter (with the exception of fertilized queens), the bees accumulate and process amounts of food stocks to be sufficient to pass the winter, because their colony is able to winter along with their queen, which can live 4-5 years.

For these reasons, bees have been used since the dawn of civilization as real pets, and were reared according to ancestral and consolidated techniques over time, applying a knowledge which is a branch of animal husbandry, beekeeping.

Although the known species of the Apidae family are currently about five thousands, the genus of bees (*Apis*) is only one. It comprises only seven species recognized as distinct species, the best known of which are *Apis to mellifera* (European honeybee), *Apis cerana* (Eastern honey bee or Asiatic honey bee), *Apis florea* (dwarf honeybee, widespread in South Asia and Southeast Asia) and *Apis dorsata* (giant honey bee of India). Only the first two species, *Apis mellifera* and *Apis cerana*, can be bred by humans and are actually made "domestic", the first one at least, from the times of ancient Egyptians.

*Apis mellifera* is the most widespread species of the genus *Apis* in the world: native to Egypt, it spread millions of years ago in the Mediterranean and in tropical Africa, and then in the presence of man it naturally populated Europe, Africa, middle East and part of Siberia. It was introduced in the seventeenth and nineteenth century also in the American continent, where it was not originally present, and it was also brought in Australia and New Zealand by the colonizers. The most well-known European subspecies of *Apis mellifera* are identified by geographic areas, separated by mountains that swarms may not overcome, where they are native and have lived with a few external contacts. There are currently 28 recognized subspecies of *Apis mellifera*, which include the black bee (*Apis mellifera mellifera*), native of northern Europe, the Italian yellow honeybee (*Apis mellifera ligustica*), which occupies most of Italy, the Carniolan bee (*Apis mellifera Carnica*) which is native to Austria and Slovenia, the Caucasian bee (*Apis mellifera caucasica*), which lives mainly in the Caucasus and Georgia, and so on. Mixed breeds and hybrids have been created by human action, either voluntary or not.

In sedentary beekeeping, hives are fixed and the area of collection of the bees does not exceed 2 or 3 km radius around the hive, which sets limits to the collection. For this reason it is also practiced nomadic beekeeping, which involves moving the hives from site to site, depending on the presence of nectar-producing plants (i.e. sugar bases to be provided to the bees). Such movements, in addition to increasing the productivity, allow the production of single-flower honeys, allowing a better offer of the final product. The transhumance is a very ancient farming technique, already practiced by nomads, who carried their hives on the back of an animal. In Italy on the Po, as in Egypt on the Nile, the hives were loaded onto special boats that sailed up the river toward regions with the most favorable honeydew. When a certain waterline was reached, the hives were full. Currently the movement of hives occurs on the road: they are loaded at nightfall (when all the bees have returned to the beehive) and are downloaded at sunrise in the new site. The hives are often downloaded and re-housed in the new area chosen for the pasture, but sometimes, in order to reduce maintenance work, the hives are left directly on vehicles equipped for this purpose.

As already noted, the bees play a vital role in the reproduction of plants with entomophilous pollination. To understand the role of bees in agriculture around the world it is enough to consider that the Food and Agriculture Organization of the United Nations (FAO) has estimated that 71 out of the 100 species of plants that provide 90% of the food worldwide are associated with bee pollination. Over the last fifty years, the agricultural production independent from insect pollination has doubled, and the agricultural production that requires pollination by insects has increased fourfold, thus indicating that world agriculture has become more pollinator-dependent. Both the FAO and other independent research organizations of this field have predicted that the economic value of pollination worldwide for agriculture and related sectors is of the order of 180 billion U.S. dollars, of which 32 billion dollars are in the United States.

It is known that the population dynamics of a bee colony is significantly influenced by the nutritional status of the colony, which controls the development, production and survival of the colony. It is also well known that the necessary food for bees are carbohydrates, proteins, lipids and vitamins: carbohydrates provide energy and are contained in nectar and honey, the other substances are present in pollen and are essential both for the production of larval food and for a balanced functioning of the bee's life. In recent years, for various reasons (including illness, poisoning, reduction of foraging areas, etc.) it has often become an indispensable requirement for the beekeeper to intervene with additional nutrition, which favors the survival of the hives or prepares them for a certain flowering (Frilli F. et al., Confronto tra gli effetti di diversi tipi di alimento per le api, Notiziario ERSA 3/2009). Sugar nutrition is the most practiced by beekeepers; it consists of delivering syrups or patties (obtained from sugars from various sources) with the aim of integrating the energy needs of the bees. In relation to the needs and to the administration time, sugar nutrition can be "stimulant", if carried out to increase the egg laying by the queen or to induce the colonies to recover after stress factors (poisonings, diseases, swarming, environmental adversity), or "compensatory", if the aim is to build up the winter stocks to avoid starvation of hives during periods of low availability.

Protein nutrition, which compensates for a lack of pollen, is a less applied nutrition technique, but sometimes it can be of vital importance to a colony of bees: in fact, the lack of pollen may entail a reduction of the bees' longevity and the reduction or total blockade of the brood, with consequent depopulation and collapse of the colonies. It should be kept in mind that in no case an artificial administration of proteins is able to completely replace pollen, and has effects only if it is carried out for a limited period of time.

Protein feeding can be done by providing the hives with (preharvested) pollen, by integrating the pollen with (up to 25% by weight of) an artificial protein component (supplemental protein nutrition) or by administering only artificial protein components (substitute protein nutrition). Very often various protein components (soybean meal, sunflower meal, yeast, milk powder, etc.) are mixed together to achieve higher nutritional value, but it is important that the total quantity of protein food preparation be between 10 and 15 wt %, as higher values can lead to toxic effects on bees.

Protein nutrition can be supplied by placing the powdered food outside the hive in special containers, or by placing the mixture inside the hive in deep frame feeders, or in patties over the combs, covered by the outer cover. In the latter case the food protein is almost always added with honey or sugar syrup until a pasty and semi-solid candy-like consistency is obtained ("protein cake").

With reference to the choice of an appropriate food for a colony of honeybees, the International Patent Application publn. No. WO 2006/073955 (The United States of America as Represented by the Secretary of Agriculture) having title "Artificial diets for domestic honey bees" discloses water dispersible preparations consisting of homogeneous mixtures of nutrients in effective amounts and proportions to support growth and development of domestic bees. The proposed formulations are considered particularly advantageous for feeding bee colonies that are moved frequently from one area to another: in the absence of sufficient natural resources, such as, e.g., during the transfers, the artificial diet preparations proposed should be able to provide all the necessary nutrients for the life of the colony. The components required in the described nutritional composition are proteins, lipids, carbohydrates, ash, cholesterol, ascorbic acid, an acidifier, an antimicrobial/antifungal agent for the preservation of the mixture and water, in the appropriate proportions. As a source of proteins and lipids soy and/or egg are proposed.

One of the major problems of the apiary is to safeguard the health of the colonies. The honey bee diseases that may develop are numerous, as a result of several pathogenetic organisms, including parasite insects, unicellular fungi, bacteria and viruses which can affect the bees in the different stages of their development.

The two best known pathogens to the beekeepers are Varroa destructor mite and Nosema apis microsporidium. The Varroa mite is an external parasite, which attaches at the body of the bee and weakens it by sucking its hemolymph. During this process the mite may also transmit viral RNA agents to the bee. The Varroa mite was found also on other pollinator insects, such as bumblebees, beetles and flies, but it can only reproduce in a colony of honeybees. Once in the colony, the female mite enters a brood cell of honey bees, giving preference to a cell containing a male brood, i.e. a drone larva. Once the cell is capped, the mite lays its eggs, after which the young mites hatch more or less at the same moment as the young bee develops, and leaves the cell with its host.

The population dynamics highlighted above shows that a large population of mites in autumn could lead to a crisis when drones rearing ceases and the mites turn to the larvae of worker bees, causing a rapid decimation of the population and often the death of the hive. For this reason the varroa mite is the parasite with the most pronounced economic impact in the apiary industry.

To fight or prevent the infestation by Varroa destructor different physical or mechanical methods are known and used to control the number of mites in the colony, as well as miticide products, both synthetic (pyrethroids, organophosphates) or of natural origin, such as oxalic acid-based preparations, or preparations based on thyme essential oil (or on synthetic thymol).

The unicellular fungus Nosema apis (more recently found in a similar form also in Apis cerana, and called in this circumstance Nosema ceranae) is characterized by a dormant state consisting of spores resistant to changes in temperature and humidity. The nosema spores, in fact, cannot be destroyed by freezing the contaminated combs. The spores are localized in intestinal epithelial cells and other cells of adult bees, where they begin the growth, heading for a series of cell divisions, invading the intestinal tract and thus causing the pathology known as nosemosis. This is manifested by dysentery evidenced by yellowish droppings outside the hive, a slow growth of the colony, disjointed wings and distended abdomen in affected individuals. The mature spores come out with the feces, contributing to the propagation of the disease.

If untreated, the nosema infection may reach the queen, causing an early replacement of the queen by workers remained healthy. The disease hinders the digestion of pollen, and therefore reduces the life of bees, and can be fought with greater difficulty in colder climates, where bees spend more time in the hive. In order to reduce the infection beekeepers use to increase the aeration in the hive and remove, as much as possible, the honey gathered by the bees for winter, feeding them with sugar solutions in replacement. The pharmacological treatments available in case of need are based on fumagillin, an antibiotic that was shown to be particularly effective for inhibiting the reproduction of spores in the host, but is not able to kill them. Spores can be inactivated, in the disinfestation of the beehive, by treating them with acetic acid or formalin.

Other pathogens for *Apis mellifera* which have been investigated for their possible involvement in recent episodes of honeybees epidemics are viral agents, including the Acute Bee Paralysis Virus (ABPV or APV), which is considered to be a common infective agent of bees, and a virus related to the previous one, described in 2004, known as Israeli Acute Paralysis Virus (IAPV) due to the fact that it was identified in Israel for the first time. It was considered that the IAPV virus plays a critical role in cases of sudden collapse of honeybees colonies infested by the parasite mite *Varroa destructor*.

Another viral pathogen recently studied for similar reasons is the invertebrate iridescent virus type 6 (IIV-6), which was identified in 2010 as a coinfectious agent in several colonies of honey bees collapsed as a result of infection by *Nosema ceranae*.

Over the last twenty years, parasite mites have certainly caused severe damage to beekeeping, also in view of the fact that they transmit harmful viruses to bees, therefore causing significant losses of colonies each year. However, while most of the deaths during the winters of 2006/07 and 2007/2008 were mainly attributed to parasitic mites, about 25-30% of dead colonies showed symptoms contrasting with mites or any other known cause.

Considering for instance the United States, in the thirty years from 1976 to 2006 there has been a drastic reduction in the number of wild bees (now almost extinct in the U.S.), and a significant, though gradual, decline in the number of families kept by beekeepers. This latter number, according to official data, declined from about 6 million in 1940 down to 2.3 million in 2008. This decline includes the cumulative losses from all factors such as urbanization, pesticide use in agriculture, acariosis and *varroa*, beekeepers' retirement and closure of businesses. However, between late 2006 and early 2007, the reduction rate has increased sharply, reaching proportions hitherto unknown, and the term "Colony Collapse Disorder" (CCD) was coined at that time to describe these sudden disappearances.

With Colony Collapse Syndrome beekeepers around the world are facing one of the toughest challenges in decades: to date a constant presence of colonies of healthy bees cannot be guaranteed, as a combination of causes, currently not fully understood, is more and more often causing mass to deaths of bees. It is a phenomenon not well known that, as noted, has been found for the first time in the colonies of bees in North America at the end of 2006, and that manifested itself in similar phenomena in Europe in subsequent years, for which families of bees (*Apis mellifera*) abruptly disappear.

Possible causes that have been suggested for CCD comprise management practices of the beekeepers, especially the stress on the colonies due to environmental changes, malnutrition and nutritional deficiencies associated with the presence of extensive monocultures, heavy use of new neonicotinoid-based pesticides and related practices and procedures for application, various pathogens such as infestation by parasite mites, *nosema* infections and viral infections (including IAPV virus), climate change, electromagnetic radiation from mobile phones or other devices created by man, genetically modified crops (GMOs) such as GM maize, new exotic pests and pathogens, decreased immunity to pathogens, and the subtle interactions between two or more of these factors. It is not yet known whether only one of these factors may be the real responsible factor, or it is a combination of factors which act independently in different areas affected by CCD, or factors that act in combination with each other, although more recent information suggest that a combination of several factors is the most likely hypothesis.

As a result of the foregoing, Colony Collapse Disorder was defined as a new syndrome of multifactorial kind which leads to the death of a very large number of colonies of bees, and that caused, from 2007 to date, losses of colonies greater than 35% per year. With regard to the diagnosis, a colony which has collapsed from CCD tends to show all of the following signs:

a) presence of a brood of abandoned larvae (usually bees do not abandon the brood until they are all hatched);
b) presence of food stores, both pollen and honey, which are not immediately robbed by other bees, when they are attacked by other insects, the attack is noticeably delayed;
c) presence of the queen in the beehive (otherwise, the phenomenon is not attributable to CCD).

At present there are no known treatments or specific solutions for the prevention and treatment of Colony Collapse Disorder, nor methods, techniques or procedures exist which the beekeeper can put in place with a reasonable expectation of success to protect his hives from such a sudden, partly unexplained event, as is the collapse of a colony from CCD.

In the light of the foregoing, the present invention is therefore aimed at providing a method for the prevention and the treatment of Colony Collapse Disorder in colonies of domestic honeybees that have not already undergone an episode of irreversible collapse, with a view to safeguarding the health of those families which have not yet been affected by the syndrome, and to improve the immune resistance and overall nutritional conditions of domestic bees.

SUMMARY OF THE INVENTION

In the framework of the research that led to the present invention, it has been considered that, although not yet fully understood in its triggering mechanisms, CCD is most likely a syndrome of multifactorial kind, and therefore an effective treatment must start from a general good health state in the colony and from the elimination of any possibility of nutritional deficiencies which may lead to reducing the immunity defenses.

Furthermore, considering that the acariasis from *Varroa destructor* and the endemic presence of *Nosema*, as well as that of viral pathogens such as IAPV and IIV-6, together with the effects of poisoning by the new generation pesticides (in particular, neonicotinoids) are among the most frequent or most likely causes of colonies' weakening, according to the present invention a method of prophylaxis and treatment of CCD in colonies of honeybees is being proposed, which method consists of regularly feeding the bees to be treated with a specifically formulated nutritional and therapeutic composition in aqueous solution, by means of an equipment designed for that purpose.

The treatment method proposed according to the invention is carried out through an automated equipment to be positioned in proximity to the hive, which allows the nebulization of a preparation (where by nebulization the transformation of a liquid into an aerosol having very fine drops is meant), the latter representing a further aspect of the invention, made with ingredients with high nutritious, tonic, antioxidant and healing activities. The invention therefore concerns both the proposed apparatus for nebulizing the therapeutic and nutrient preparation and the formulation in terms of components of the preparation itself.

The solution or aqueous suspension to be distributed to the bees according to the invention is obtained through the optimal combination of: a) nutrient and tonic ingredients mostly based on powdered milk and/or yeast, sugar and lower organic acids, b) natural antioxidants and antiseptics having high activity, contained in extracts of some plants known for their herbal properties, and c) therapeutic substances for bees, such as the extract of *Thymus vulgaris*, having the ability of preventing or countering the proliferation of ectoparasite mites and fungal forms harmful to bees. The combination of ingredients proposed is able to prevent nutritional deficiencies, to safeguard the health conditions of the colonies treated and at least partially counteract the effect of contamination by pesticides such as neonicotinoids, thus drastically reducing the risk of contracting CCD or mitigating the effects thereof.

BRIEF DESCRIPTION OF THE DRAWINGS

The specific features of the invention, as well as the advantages of the same and their operational modes, will be apparent with reference to the detailed description presented below, and to some specific embodiments of the relevant dispensing device, illustrated by way of example in the accompanying drawings. In the accompanying drawings.

DETAILED DESCRIPTION OF THE INVENTION

Figure 1:
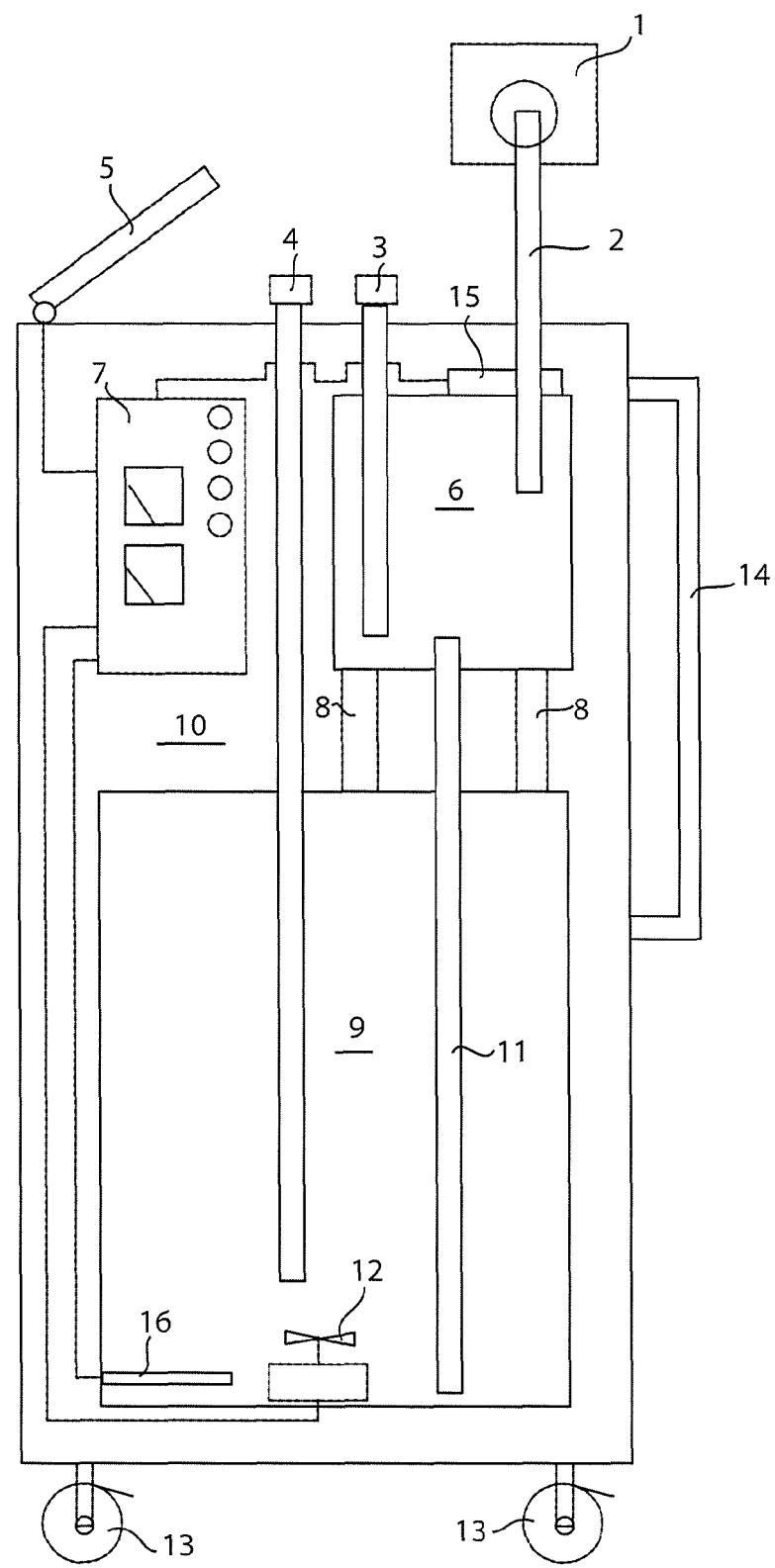
FIG. 1 is a functional scheme of a first embodiment of the dispensing apparatus according to the invention for the automated delivery of a therapeutic and nutrient preparation for CCD to the colonies of bees to be treated.

Therefore, the present invention specifically provides an automated equipment—to be positioned in the proximity of the hive—for the prevention and treatment of Colony Collapse Disorder (CCD) through the administration of nutrient and therapeutic substances to bee colonies to be treated, said apparatus comprising a boxlike container made of a material resistant to atmospheric agents, which accommodates in its interior at least a first liquid-tight reservoir fitted with a stirrer, and accessible from the outside through a first inlet neck, a nebulizing device for a liquid solution or suspension of nourishment contained in said first reservoir, means for dispensing the liquid solution or suspension nebulized into micrometric drops outside the apparatus, and a control unit programmed for timing the delivery of the solution or suspension to the outside, for dosing the amount of solution or suspension dispensed and for emitting warning signals in case of malfunctioning of the apparatus or reduction of the liquid solution or suspension contained in the first reservoir below a preset level, said apparatus being powered in DC by energy supplied by a solar panel placed on the exterior of said boxlike container and electrically connected to said control unit.

According to a preferred embodiment of the apparatus of the invention, the means for dispensing the nebulized liquid solution or suspension to the exterior include a container or feeding chamber accessible to the bees but sheltered from the external environment, for example similar to those containers used as "feeders" to be positioned on top of the outer cover in conventional hives, but with an entrance for the bees provided from the outside. It is also possible to provide, above the container/feeder itself, a cover having the function of a sunscreen, preferably colored in bright and floral colors, in order to better attract bees to the food source.

According to other preferred embodiments, the means for dispensing the nebulized liquid solution or suspension outside of the apparatus also include a telescopic tube extensible in length upwards, placed between the boxlike container of the apparatus and said container or feeding chamber, which allows to adjust the height of the point of delivery of the nutritious and therapeutic preparation of the invention.

Preferably, the proposed apparatus according to the invention comprises a second reservoir inside said boxlike container, having smaller volume than the first reservoir, in communication with it and separately accessible from the outside through a second inlet neck. The two separate accesses permit to reintegrate independently an aqueous concentrated solution or suspension of the nutritious and therapeutic preparation according to the invention through the second inlet neck, while the first inlet neck is used only for the connection to the water supply.

The boxlike container of the apparatus proposed is conveniently made of material resistant to atmospheric agents, for example similar to the material of the hives near which it must be placed, and it is preferably externally colored with one or more colors that are attractive to pollinator insects, such as purple, blue, red or green. Preferably, said container is made of seasoned spruce wood, externally painted in the above mentioned colors.

To further facilitate the management of the automated treatment, the apparatus according to the invention may comprise further control devices in addition to those already mentioned, compatibly with the cost of such equipment. In particular, it may comprise one or more temperature and/or pH sensors, or multiparameter sensors, located inside the main reservoir, and the control unit may be programmed to monitor the measured values of the relative magnitudes and to emit alarm signals in the event that these values go beyond the set limits.

As it has to be positioned on the ground in the proximity of the bees colonies to be treated, the apparatus according to the invention preferably comprises four wheels placed below the boxlike container, and one or more handles for manually positioning said apparatus, so as to enable the beekeeper to move it in the most favorable place in relation to the hives, the water supply location, the position of the sun, and other requirements that may vary during the season or depending on other events.

Figure 2:
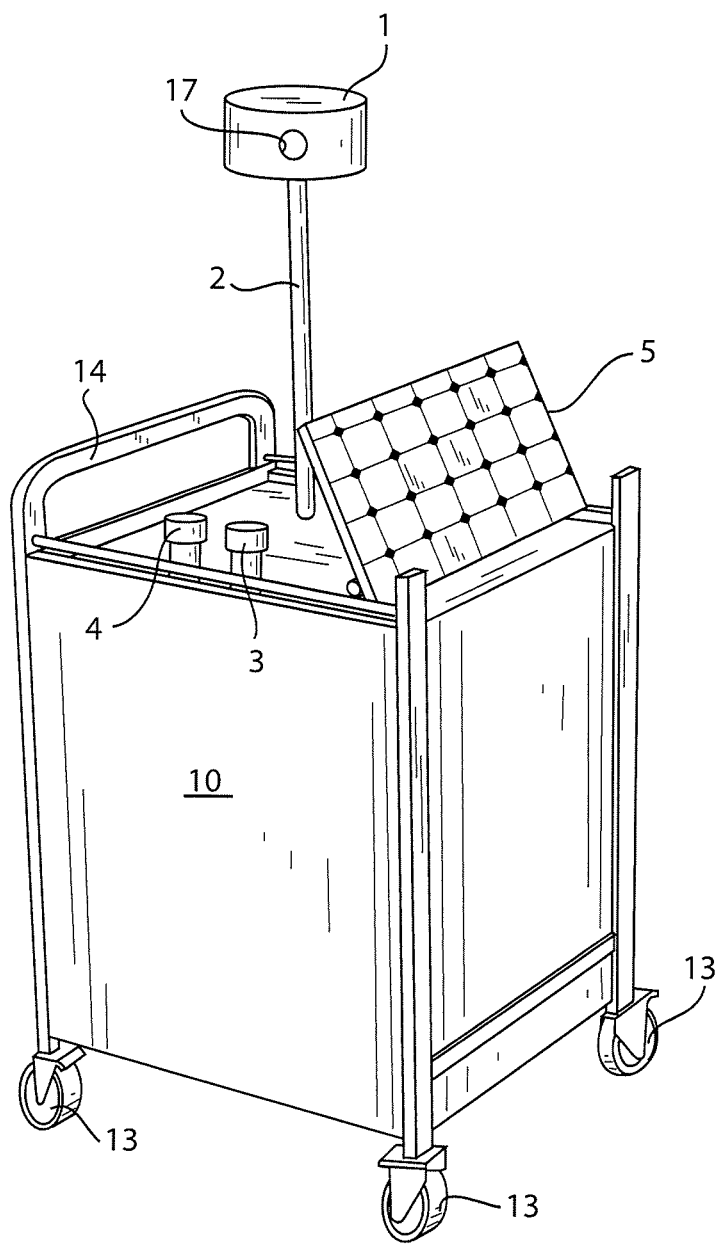
FIG. 2 is a perspective view of a second embodiment of the dispensing apparatus for a therapeutic ad nutrient preparation for CCD according to the invention.

The apparatus according to the invention is also described in the two to exemplary embodiments illustrated in FIGS. 1 and 2 of the accompanying drawings (where corresponding elements are indicated with the same reference numerals). The apparatus consists of a special and automated nebulizing system to be installed in the proximity of the colonies or hives in order to facilitate the accessibility to the nebulized liquid preparation, through the apparatus, by the families of bees to be subjected to the treatment.

The system is composed of a box or container (10), for example equipped with wheels (13) and handle (14) to allow its positioning, and having a color suited to attract the bees and/or to be viewed by them, for example, in purple, blue, red or yellow. The container (10) can be realized in different materials, possibly recyclable, such as seasoned spruce wood or other timber suitable for the outdoor permanence and for the exposure to sunlight and rain.

Inside the container (10) a first gas-tight reservoir (6) is housed, having a volume from a minimum of 2 liters to a maximum of 20 liters, in which there is poured, through the inlet neck (3), the concentrate prepared according to the invention with selected ingredients, later detailed, and that allows the correct dosage of the ingredients themselves.

In a second gas-tight reservoir (9), having a volume from a minimum of 20 liters to a maximum of 35 liters, drinking water is loaded through the inlet neck (4), possibly water with low hardness, by which the content of the first reservoir (6) will be diluted. Alternatively, a single reservoir may be used, in which both water and the therapeutic and nutritious preparation to be diluted are loaded.

In the case where the reservoirs designed are two, they are connected together through a pipe (11) and are supported on one another by means of supporting elements (8). On the bottom of the larger reservoir (9) (in the case of two reservoirs) or of the only reservoir (in the case of a single reservoir) there is a mixer (12) which is activated for short periods of time (generally few minutes) and allows the preparations to be maintained mixed thus avoiding any form of sedimentation on the bottom.

The periodic distribution of the preparation according to the invention to the bees to be treated is carried out by nebulization of the preparation through special dispensing nozzles, preferably placed within a feeder-type container (1) similar to those normally used in the apiary in covercombs, but accessible to the bees from the outside, for example, through the opening (17). The nebulization occurs through a nebulizing device (15) powered in DC, by means of rechargeable batteries which in turn are fed by a 5 W to 15 W solar panel (5), installed on the equipment, working at from 4.5 volts up to a maximum of 12 volts. The electrical nebulization system that pressurizes the contents of the reservoirs (6) and (9), or the one reservoir, is equipped with a telescopic tube (2) having, for example, a length up to 150 cm. The telescopic tube (2) allows to place at the optimum height the dispensing nozzles, which emit a micrometer mist (aerosol) consisting of the preparation in aqueous solution or suspension according to the invention.

As already noted, the energy required to operate the equipment is supplied by a solar panel (5), which allows to use the equipment also in open country and where there is no available fixed power supply. Therefore, the operator using the equipment, after placing it in the optimal place in the proximity of the hives, has only to fill the reservoir with water and pour the mixture according to the invention. The preparation should be refilled approximately every 2-3 months, while the water level is not to be reintegrated more than once a month.

Thanks to an electronic control system (7) present in the apparatus and to a programmed timer, the nutritious and therapeutic preparation according to the invention is sprayed periodically and made available to the bees in micronized drops of solution or suspension. The control system (7) also allows to check the water and the nutritious and therapeutic preparation levels, and notifies the user, by means of a light and/or sound signal, and by sending telephonic messaging and/or e-mail, when a reservoir reaches the minimum level. The electronic control system (7) indicates in the same way the nebulizer module efficiency (in particular, the possible clogging of the nozzles), by signaling an abnormal electric absorption by the nebulizing system or, alternatively, by means of a pressure device which shows an increase of pressure at the nebulizer itself, which is a symptom of inlet nozzles clogging.

The control system (7) also allows to detect and report general anomalies of the timing system (which may be digital or mechanical with mobile switches), of the solar panel (5) functioning or the batteries charge levels. The control system (7), which can also be a simple PLC (programmable logic controller), acquires the data of the multiparameter probe (16), with alarm for temperatures below 0° C. and possible verification of the pH of the solution to be nebulized, to control the exact dosage of the components of the preparation according to the invention in relation to water.

The control system (7) can be further equipped with an interface for remote control and verification that allows programming or management of the alarm signals through smartphone applications, so as to have access to data 24 hours a day, and especially to be able to check the proper functioning of the equipment.

The aqueous solution or suspension of the present invention to be used for being dispensed through the automated apparatus described above is made by the combination of ingredients selected to provide nourishment in calibrated proportions, consisting of sugars, protein foods such as yeast and milk powder, essential oils containing antioxidant active ingredients and having high tonic and healing effect.

Therefore, the invention further concerns a liquid solution or suspension of nourishment deliverable in a nebulized form through the automated apparatus proposed, for the prevention and treatment of Colony Collapse Disorder (CCD), characterized in that it comprises, in a single aqueous solution or suspension:

a) tonic and nutritious ingredients, mainly consisting of: milk powder and/or yeasts; sugars and lower organic acids;

b) natural antioxidants and antiseptics contained in the extracts of one or more aromatic or medicinal plants selected from: *Crocus sativus*, Pelargonium *graveolens, Monarda citriodora, Myristica fragrans, Origanum vulgare* and *Origanum majorana*; and c) curative substances for bees, selected from thymol, oxalic acid, extracts of *Thymus vulgaris*, extracts of *Aloe arborescens*, extracts of *Beta vulgaris* cv. *altissima* and mixtures of two or more of the same.

More specifically, the substances used in the preparation according to the invention are the following:

A. Nutrient and Tonic Substances

1) Yeast, for example, baker's yeast, and/or milk powder, of which the bees are very fond. The level of proteins of the same is about 50% with a fat content around 7%. Yeasts and milk are the most complete in terms of amino acids and are rich in B vitamins.

2) Sugar of the glucose or fructose type to increase the palatability of the protein element to be administered. It is possible to add pollen and/or icing sugar (sucrose) in an amount ranging from 5% to 15% on the total dry weight of the formulation. As nutrients vitamin E and essential amino acids extracted from *Aloe arborescens* have also been used, which are listed below among the substances having curative activity.

3) Acetic acid and/or lower carboxylic or dicarboxylic acids, $C_2$-$C_6$. Aacetic acid, tartaric acid and citric acid have the ability to cleave the molecules of sucrose, promoting assimilation by the bees. Also, said acids are antifungals useful in combating the presence of the fungus *Nosema* and other fungal forms. Specifically, the formulation may contain acetic acid at a maximum concentration of 6% by weight. A source of ascorbic acid (vitamin C), such as lemon juice (which contains it, in addition to the most abundant citric acid), may be included in the formulation as a vitamin compound, as well as an antioxidant.

4) Among the measures taken to avoid the crystallization of the concentrated solution, one part of water and two parts of sugar can be brought to a boil for fifteen minutes and add at the end a 5% of glycerol and/or propylene glycol (calculated on the total weight of the concentrated formulation). This also has the advantage of lowering the freezing point of the entire composition, thus preventing the freezing of the preparation during the winter B. Highly Active Antioxidants and Antiseptics Essential oils with a high content of antioxidants and/or antiseptics were extracted and added to the formulation, such as carotenoids of the type of crocetin, crocin and picrocrocin extracted from flowers and/or stigmas of saffron (extracts of *Crocus sativus*); essential oils as limonene, e.g. extracted from lemon; geraniol, citronellol, terpineol and linalool, extracted from Pelargonium *graveolens* (geranium), or from Monarda *citriodora* var. *citriodora; myristicin, elemicin, geraniol and/or safrole and other aromatic ethers extracted from Myristica fragrans* (nutmeg); carvacrol, thymol and other minor phenols extracts from *Origanum vulgare* (ssp *hirtum*); and terpenes type terpineol, borneol, sabinene and linalool, extracted from *Origanum majorana*.

These active ingredients can be extracted for example from the plant species above and usually have a purity exceeding 55%, or they can be made synthetically.

C. Other Therapeutic Substances

To counteract and/or prevent mites, harmful fungal forms, viruses including the IIV6 and IAPV and side effects of neonicotinoids biologically active substances contained in *Thymus vulgaris* (common thyme) and those contained in *Aloe arborescens* (a species of *Aloe* less common of *Aloe vera*, but richer in biological active substances) were used. The first one, whose essential oil is already widely used in beekeeping, contains two phenolic compounds with biocidal activity, thymol and carvacrol, as well as cineol, borneol and other terpene compounds.

The second one, *Aloe arborescens*, contains many biologically active compounds, including acemannan (a mucopolysaccharide known for its antiviral activity, having an immunomodulator action) and anthraquinones, including aloin and emodin, beta-sitosterol, in addition to acetylsalicylic acid. As already noted, the extracts of this plant also contain all of the essential amino acids and vitamin E.

Moreover, a good activity was observed according to the invention with the use of extracts of common beet or *Beta vulgaris* cv *altissima* (sugar beet), containing flavonoids, trimethylglycine, compounds with antioxidant activity, oxalic acid and B vitamins.

These extracts can also be added with oxalic acid in a quantity not exceeding 1% of the total of the concentrated formulation, for increasing the disinfecting effect in synergy with the natural compounds cited.

Preparation of the Concentrated Solution or Suspension—

The concentrated solution or suspension, which must be subsequently diluted with water to reach the desired concentrations of the various ingredients, is prepared by the sequential addition of the various nutrients, followed by the antioxidants and the curative compounds, mixing with a bench stirrer in order to obtain an homogeneous solution (or suspension).

According to some specific embodiments of the nebulizable solution or suspension of the invention, such nutrients and tonic ingredients included in the formulation consist of milk powder, glucose and/or fructose, acetic acid, tartaric acid and citric acid. Preferably, as already noted, the formulation is added with a small amount of glycerin to avoid crystallization of the concentrated intermediate solution.

Preferably, the solution or suspension proposed contains the following aromatic and medicinal plant extracts in combination, with functions of primary antioxidants and/or antiseptics: *Crocus sativus* extract; *Pelargonium graveolens* extract; *Myristica fragrans* extract; *Origanum vulgare* extract and *Origanum majorana* extract. Optionally, to the quoted extracts it is also added the extract of *Monarda citriodora*

Additionally, the proposed solution or suspension contains, as curative substances for bees, *Thymus vulgaris* extracts, extracts of *Aloe arborescens* and oxalic acid, and, according to a preferred embodiment, also extract of *Beta vulgaris* cv. *altissima*.

An exemplary formulation of the nutritious and therapeutic preparation of the invention is shown in the following table, showing the preferred concentrations ranges for the various ingredients.

TABLE 1

Preferred concentrated formulation

| INGREDIENTS | PREFERRRED CONCENTRATIONS (% by weight) |
|---|---|
| Milk powder | 5-10 |
| Distilled water | 28-33 |
| Glucose and/or fructose | 53-60 |
| Vinegar | 0.8-1.2 |
| Glycerine | 0.4-0.6 |
| Liquid lemon sauce | 0.4-0.6 |
| *Crocus sativus* (crocus) | 0.05-0.11 |
| *Pelargonium graveolens* (geranium) | 0.05-0.08 |
| *Monarda citriodora* (monarda) | 0.00-0.08 |
| *Myristica fragrans* (nutmeg) | 0.08-0.12 |
| *Origanum vulgare* (oregano) | 0.08-0.12 |
| *Origanum majorana* (marjoram) | 0.08-0.12 |
| Thymol | 0.00-0.04 |
| *Thymus vulgaris* (thyme) | 0.03-0.07 |
| *Aloe arborescens* | 0.10-0.20 |
| *Beta vulgaris* (common beet) | 0.00-0.30 |
| Oxalic acid | 0.00-0.10 |

According to another aspect complementary to the above, the present invention consists in a method of treatment of domestic bees colonies for the prevention and treatment of Colony Collapse Disorder through the administration of nutritious and therapeutic substances, which method consists in the use the automatized apparatus of the invention described above for dispensing in a spray form an aqueous liquid solution or suspension containing:

a) tonics and nutritious ingredients, mainly consisting of: milk powder and/or yeasts, sugars and lower organic acids;

b) natural antioxidants and antiseptics contained in the extracts of one or more aromatic or medicinal plants selected from: *Crocus sativus, Pelargonium graveolens, Monarda citriodora, Myristica fragrans, Origanum vulgaris* and *Origanum majorana*; and c) medicinal substances for bees, selected from thymol, oxalic acid, extracts of *Thymus vulgaris, Aloe arborescens* extracts, extracts of *Beta vulgaris* cv. *altissima* and mixtures of two or more thereof.

In the method of treatment according to the invention, preferred solutions are those in which such nutrient ingredients and tonics consist of milk powder, glucose and/or fructose, acetic acid, tartaric acid and citric acid. Moreover, as already noted, such nutrient ingredients and tonics preferably comprise also glycerin.

According to some preferred embodiments of the method of treatment and prophylaxis of the invention, the liquid solution or suspension contains the extracts of aromatic or medicinal herbs already mentioned, in combination: *Crocus sativus* extract; *Pelargonium graveolens* extract; *Myristica fragrans* extract; *Origanum vulgare* extract and *Origanum majorana* extract. Moreover, as already noted, the liquid solution or suspension may comprise in addition extract of Monarda *citriodora*.

Still according to some specific embodiments of the method of prophylaxis and therapy of the invention, said substances curative for the bees are preferably extracts of *Thymus vulgaris*, extracts of *Aloe arborescens* and oxalic acid. In addition, a preferred variant also contains the extract of *Beta vulgaris* cv. *altissima*.

By way of examples, which are not to be considered limitative but are useful to clarify the therapeutic and prophylactic measures for CCD proposed according to the invention, two formulations of exemplary solutions are reported in the following, which are suitable to be dispensed through the device proposed according to the method of the invention. The results of experiments conducted on the same formulations in field tests are reported as well.

Example 1

Concentrated Nourishing, Antioxidant and Curative Formulation No. 1

A first formulation to produce one liter of concentrated preparation to be diluted in 30 liters of water for the final spraying on a number of hives from 10 up to a maximum of 15 contained the following ingredients in the following proportions.
A) Nutrients and tonics—to a total of 425 ml:

| | |
|---|---|
| aqueous solution at 15% by weight of milk powder | 80 ml |
| aqueous solution at 90% by weight of sugar | 260 ml |
| aqueous acetic acid at 6% by weight | 20 ml |
| glycerin | 50 ml |
| tartaric acid | 5 ml |
| citric acid | 10 ml |

B) Antioxidants—to a total of 255 ml: Essential oils in aqueous solution:

| | |
|---|---|
| *Crocus sativus* | 55 ml, |
| *Pelargonium* | 45 ml, |
| *Monarda citriodora* | 35 ml, |
| *Myristica fragrans* | 45 ml, |
| *Origanum vulgare* ssp *hirtum* | 40 ml, |
| *Origanum majorana* | 35 ml; |

C) Curative substances—to a total of 320 ml:
   Essential oils in aqueous solution:

| | |
|---|---|
| *Thymus vulgaris* | 100 ml; |
| *Aloe arborescens* | 175 ml; |
| *Beta vulgaris* cv *altissima* | 25 ml; |
| aqueous oxalic acid at 3% by weight | 20 ml. |

| Nutrients contained in the milk | FORMULA I |
|---|---|
| lipids | 2.61 g |
| proteins | 2.39 g |
| sugars | 13.52 g |

The process to obtain the solution involves the sequential addition of the various nutrients in the order as indicated above, followed by the antioxidants and ending with the addition of the curative substances. Once added within a container, they are stirred at room temperature for 5-10 minutes with a bench stirrer in order to obtain a homogeneous solution of 1000 ml. At this point the preparation is ready to be further diluted with water, preferably of low hardness, or with demineralized water.

Example 2

Concentrated Nourishing, Antioxidant and Curative Formulation No. 2

A second formulation to make one liter of concentrated preparation to be diluted in 29 liters of water for the final spraying on a number of hives from 10 up to a maximum of 15 contained the following ingredients in the following proportions.
A) Nutrients and tonics—to a total of 425 ml:

| | |
|---|---|
| aqueous solution at 15% by weight of milk powder | 70 ml |
| aqueous solution at 90% by weight of sugar | 250 ml |
| aqueous acetic acid at 6% by weight | 20 ml |
| glycerin | 50 ml |
| citric acid | 10 ml |

B) Antioxidants—to a total of 245 ml:
   Essential oils in aqueous solution:

| | |
|---|---|
| *Crocus sativus* | 55 ml, |
| *Pelargonium* | 35 ml, |
| *Myristica fragrans* | 55 ml, |
| *Origanum vulgare* ssp *hirtum* | 75 ml, |
| *Origanum majorana* | 25 ml; |

C) Curative substances—to a total of 355 ml:
   Essential oils in aqueous solution:

| | |
|---|---|
| *Thymus vulgaris* | 90 ml; |
| *Aloe arborescens* | 245 ml; |
| oxalic acid at 3% by weight in aqueous solution | 20 ml. |

| Nutrients contained in the milk | FORMULA II |
|---|---|
| lipids | 2.28 g |
| proteins | 2.03 g |
| sugars | 11.83 g |

The process to obtain the final solution involves the sequential addition of the various nutrients in the order as indicated above, followed by the antioxidants and ending with the addition of the curative substances. Once added within a container, they are stirred at room temperature for 5-10 minutes with a stirrer bench in order to obtain a homogeneous solution of 1000 ml. At this point the preparation is ready to be further diluted with water, preferably of low hardness, or with demineralized water.

Experimentation in the Field

Tests have been made since 2009 in Italy, in Tuscany region at a location about 200 meters above sea level. The apparatus according to the invention has been positioned in the proximity of 10 active spruce hives, about 3 meters from the same and was fed continuously with batches of nutritious and therapeutic preparation formulated as in Example 1, and thereafter with batches of preparation formulated as in Example 2.

This equipment has been active until the early months of 2011 and in the colonies there were no problems related to CCD, while in other domestic bees colonies in the vicinity there was an average loss of more than 20% over the same two years. At the end of 2010 the number of colonies in the apiary subjected to treatment according to the invention was increased up to a total of 14, with a net increase of 40%.

At the beginning of 2011 the apparatus according to the invention was removed, and as of late March 2011, the same hives were gradually affected by the depopulation of CCD, and their total number was reduced to only four units in the month of July 2011. Thus, this finding confirms the initial hypothesis that the treatment method of the invention, as implemented through the proposed automatic nebulizing equipment properly positioned in the vicinity of colonies of honey bees to be treated, and fed with the described nutrient, antioxidant and curative formulation is effective to prevent and fight Colony Collapse Disorder.

From the foregoing there follows that the prophylactic and therapeutic solution proposed according to the invention, besides countering the aforementioned problems of mites, fungi and IIV-6 and IAPV viruses, also provides a remedy to the shortage of food and tonics, and counters the negative effects of poisoning by the new generation pesticides, allowing to prevent and fight the onset of Colony Collapse Disorder.

The present invention has been described with particular reference to some embodiments thereof but it should be understood that changes and modifications may be made by those skilled in the art without departing from the scope of the invention as described in the appended claims.

The invention claimed is:

1. A method for prevention and treatment of Colony Collapse Disease (CCD) by administering nutrients and therapeutic substances to bee colonies to be treated, comprising delivering a liquid solution or suspension in a form of spray, the liquid solution or suspension comprising:

a) a nutrition composition comprising a sugar, a $C_2$-$C_6$ organic acid, and milk powder, and optionally yeasts;
b) an antioxidant and antiseptic composition comprising an extract of *Origanum vulgare* and an extract of at least one plant selected from the group consisting of *Crocus sativus, Pelargonium graveolens, Monarda citriodora, Myristica fragrans*, and *Origanum majorana*; and
c) a medicinal composition for bees comprising at least one selected from the group consisting of thymol and extracts of *Thymus vulgaris*, and at least one selected from the group consisting of extracts of *Aloe arborescens*, oxalic acid, extracts of *Beta vulgaris* cv. *altissima*, and mixtures thereof.

2. The method for prevention and treatment according to claim 1, wherein said nutrition composition comprises milk powder, acetic acid, tartaric acid, citric acid and one selected from the group consisting of glucose, fructose and a mixture of glucose and fructose.

3. The method for prevention and treatment according to claim 2, wherein said nutrition composition further comprises glycerin.

4. The method for prevention and treatment according to claim 1, wherein said liquid solution or suspension comprises an extract of *Origanum vulgare* and an extract of at least two selected from the group consisting of *Crocus sativus* extract; *Pelargonium graveolens* extract; *Myristica fragrans* extract; and *Origanum majorana* extract.

5. The method for prevention and treatment according to claim 4, wherein said liquid solution or suspension further comprises extract of *Monarda citriodora*.

6. The method for prevention and treatment according to claim 1, wherein said medicinal composition for bees comprises extracts of *Thymus vulgaris*, extracts of *Aloe arborescens* and oxalic acid.

7. The method for prevention and treatment according to claim 6, wherein said medicinal composition for bees further comprises extract of *Beta vulgaris*.

* * * * *